US00PP22376P2

(12) United States Plant Patent
Kosick

(10) Patent No.: US PP22,376 P2
(45) Date of Patent: Dec. 20, 2011

(54) ***GERANIUM* PLANT NAMED 'BLUSHING TURTLE'**

(50) Latin Name: ***Geranium* hybrid**
Varietal Denomination: Blushing Turtle

(76) Inventor: Karin Kosick, Nanoose Bay (CA)

( * ) Notice: Subject to any disclaimer, the term of this patent is extended or adjusted under 35 U.S.C. 154(b) by 0 days.

(21) Appl. No.: 12/804,005

(22) Filed: Jul. 12, 2010

(51) Int. Cl.
*A01H 5/00* (2006.01)

(52) U.S. Cl. ..... Plt./324
(58) Field of Classification Search ..... Plt./324
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Geranium* plant named 'Blushing Turtle', characterized by its upright, low spreading and rounded plant habit; vigorous growth habit; freely branching habit; large purple violet-colored flowers with red purple-colored venation; long and continuous flowering period; and good garden performance.

1 Drawing Sheet

Botanical designation: *Geranium* hybrid.
Cultivar denomination: 'BLUSHING TURTLE'.

BACKGROUND OF THE INVENTION

The present invention relates to a new and distinct cultivar of *Geranium* plant, botanically known as *Geranium* hybrid, and hereinafter referred to by the name 'Blushing Turtle'.

The new *Geranium* plant is a product of a planned breeding program conducted by the Inventor in Nanoose Bay, British Columbia, Canada. The objective of the breeding program is to create new repeat flowering *Geranium* plants with large flowers and drought tolerance.

The new *Geranium* plant originated from a cross-pollination made by the Inventor during the summer of 1999 in Nanoose Bay, British Columbia, Canada of a unnamed seedling selection of *Geranium sanguineum,* not patented, as the female, or seed, parent with either *Geranium×oxonianum* 'Julie Brennan', not patented, or an unnamed selection of *Geranium asphodeloides,* not patented, as the male, or pollen, parent. Pollen from both *Geranium×oxonianum* 'Julie Brennan' and an unnamed selection of *Geranium asphodeloides* was collected and used to cross-pollinate the unnamed seedling selection of *Geranium sanguineum.* The new *Geranium* plant was discovered and selected by the Inventor as a single flowering plant within the progeny of the stated cross-pollination in a controlled environment in Nanoose Bay, British Columbia, Canada in May, 2002.

Asexual reproduction of the new *Geranium* plant by cuttings in a controlled environment in Nanoose Bay, British Columbia, Canada since March, 2003, has shown that the unique features of this new *Geranium* plant are stable and reproduced true to type in successive generations.

SUMMARY OF THE INVENTION

Plants of the new *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Blushing Turtle'. These characteristics in combination distinguish 'Blushing Turtle' as a new and distinct cultivar of *Geranium* plant:

1. Upright, low spreading and rounded plant habit.
2. Vigorous growth habit.
3. Freely branching habit.
4. Large purple violet-colored flowers with red purple-colored venation.
5. Long and continuous flowering period.
6. Good garden performance.

Plants of the new *Geranium* differ primarily from plants of the female parent selection in the following characteristics:

1. Plants of the new *Geranium* are larger than plants of the female parent selection.
2. Plants of the new *Geranium* have larger leaves than plants of the female parent selection.
3. Plants of the new *Geranium* and the female parent selection differ in flower color as plants of the female parent selection have purple-colored flowers.

Plants of the new *Geranium* differ primarily from plants of either of the possible male parents in the following characteristics:

1. Plants of the new *Geranium* have larger leaves than plants of either of the possible male parents.
2. Plants of the new *Geranium* have larger flowers than plants of either of the possible male parents.
3. Plants of the new *Geranium* flower for a longer period of time than either of the possible male parents.

Plants of the new *Geranium* can be compared to plants of *Geranium sanguineum* 'John Elsley', not patented. In side-by-side comparisons conducted in Nanoose Bay, British Columbia, Canada, plants of the new *Geranium* differed primarily from plants of 'John Elsley' in the following characteristics:

1. Plants of the new *Geranium* were larger than plants of 'John Elsley'.
2. Plants of the new *Geranium* had larger leaves than plants of 'John Elsley'.

3. Plants of the new *Geranium* and 'John Elsley' differed in flower color as plants of 'John Elsley' had dark magenta-colored flowers.

Plants of the new *Geranium* can be compared to plants of *Geranium* 'Dilys', not patented. In side-by-side comparisons conducted in Nanoose Bay, British Columbia, Canada, plants of the new *Geranium* differed primarily from plants of 'Dilys' in the following characteristics:

1. Plants of the new *Geranium* were larger than plants of 'Dilys'.
2. Plants of the new *Geranium* had larger flowers than plants of 'Dilys'.
3. Plants of the new *Geranium* and 'Dilys' differed in flower color as plants of 'Dilys' had red purple-colored flowers.

BRIEF DESCRIPTION OF THE PHOTOGRAPHS

The accompanying colored photographs illustrate the overall appearance of the new *Geranium* plant, showing the colors as true as it is reasonably possible to obtain in colored reproductions of this type. Colors in the photographs may differ slightly from the color values cited in the detailed botanical description which accurately describe the colors of the new *Geranium* plant.

The photograph at the bottom of the sheet comprises a side perspective view of a typical flowering plant of 'Blushing Turtle' grown in a container.

The photograph at the top of the sheet is a close-up view of typical flowers and leaves of 'Blushing Turtle'.

DETAILED BOTANICAL DESCRIPTION

The aforementioned photographs and following observations, measurements and values describe plants grown during the spring in 20-cm containers in a polyethylene-covered greenhouse in Lancaster, Pa. During the production of the plants, day temperatures ranged from 16° C. to 35° C. and night temperatures averaged 2° C. Plants were one year old when the photographs and the description were taken. In the detailed description, color references are made to The Royal Horticultural Society Colour Chart, 2007 Edition, except where general terms of ordinary dictionary significance are used.

Botanical classification: *Geranium* hybrid 'Blushing Turtle'.

Parentage:

*Female, or seed, parent.*—Unnamed seedling selection of *Geranium sanguineum,* not patented.

*Male, or pollen, parent.*—Either *Geranium×oxonianum* 'Julie Brennan', not patented, or an unnamed selection of *Geranium asphodeloides,* not patented.

Propagation:

*Type.*—By cuttings.

*Time to initiate roots, summer.*—About ten days at 23° C.

*Time to initiate roots, winter.*—About eight days at 8° C.

*Time to produce a rooted young plant, summer.*—About 16 days at 23° C.

*Time to produce a rooted young plant, winter.*—About 30 days at 8° C.

*Root description.*—Medium in thickness, fibrous; burnt umber in color.

*Rooting habit.*—Freely branching; moderately dense.

Plant description:

*Plant and growth habit.*—Hardy herbaceous perennial; upright and low spreading plant habit, rounded plant shape; vigorous growth habit.

*Plant height.*—About 15.5 cm.

*Plant width.*—About 50 cm.

*Branching habit.*—Freely branching habit with about 20 lateral branches per plant.

*Lateral branch length.*—About 26 cm.

*Lateral branch diameter.*—About 2.5 mm.

*Internode length.*—About 5 cm.

*Lateral branch aspect.*—Outwardly and horizontally spreading.

*Lateral branch strength.*—Strong.

*Lateral branch texture.*—Pubescent.

*Lateral branch color.*—Close to 146C.

Foliage description:

*Arrangement.*—Opposite, simple.

*Length.*—About 5.6 cm.

*Width.*—About 6 cm.

*Shape.*—Deeply dissected.

*Apex.*—Acute.

*Base.*—Sagittate.

*Margin.*—Five palmate lobes; lobes biserrate.

*Venation pattern.*—Palmate; reticulate.

*Texture, upper and lower surfaces.*—Pubescent.

*Color.*—Developing leaves, upper surface: Close to 137C. Developing leaves, lower surface: Close to 147B. Fully developed leaves, upper surface: Close to N137A; venation, close to 147B. Fully developed leaves, lower surface: Close to 147B; venation, close to 147B.

*Petiole.*—Length: About 3.2 cm. Diameter: About 1 mm. Texture, upper and lower surfaces: Pubescent. Color, upper and lower surfaces: Close to 146B.

Flower description:

*Flowering habit.*—Single axillary slightly funnelform rotate flowers; freely flowering habit with about 5 to 6 open and developing flowers per lateral branch.

*Fragrance.*—None detected.

*Flowering season and flower longevity.*—In Nanoose Bay, British Columbia, Canada, flowering is continuous from spring until autumn; individual flowers last about three to four days on the plant; corollas not persistent, however sepals and gynoecium are persistent.

*Flower bud length.*—About 1.3 cm.

*Flower bud diameter.*—About 6 mm.

*Flower bud shape.*—Ovoid.

*Flower bud color.*—Close to N81B.

*Flower diameter.*—About 3.7 cm.

*Flower height.*—About 1.6 cm.

*Petals.*—Quantity per flower: Five in a single whorl. Length: About 2.3 cm. Width: About 1.8 cm. Shape: Obcordate. Apex: Cordate. Base: Acute. Margin: Entire. Texture, upper and lower surfaces: Smooth, glabrous. Color: When opening and fully opened, upper surface: Close to N80B; venation, close to 71A. When opening and fully opened, lower surface: Close to N81D.

*Sepals.*—Quantity per flower: Five, arranged in a single whorl. Length: About 1.2 cm. Diameter: About 4 mm. Shape: Elliptical. Apex: Acuminate. Base: Truncate. Margin: Entire. Texture, upper surface: Smooth, glabrous. Texture, lower surface: Pubescent. Color, upper surface: Close to 146C. Color, lower surface: Close to 146B.

*Peduncles.*—Length: About 9 cm. Diameter: About 1 mm. Aspect: About 30° to 45° from the stem axis. Strength: Strong. Texture: Pubescent. Color: Close to 146C.

*Reproductive organs.*—Androecium: Stamen quantity per flower: About ten. Filament length: About 7 mm. Filament color: Close to 76A to 76B. Anther length: About 3.5 mm. Anther shape: Oblong. Anther color: Close to 85C. Pollen amount: Scarce. Pollen color: Close to NN155B. Gynoecium: Pistil quantity per flower: One. Pistil length: About 1.1 cm. Stigma shape: Five-parted and recurving. Stigma color: Close to N80C. Style length: About 5 mm. Style color: Close to N78C. Ovary color: Close to 147B.

*Seed/fruits.*—Seed and fruit development have not been observed.

Disease/pest resistance: Plants of the new *Geranium* have been observed to be resistant to mildews. Plants of the new *Geranium* have not been observed to be resistant to pests and other pathogens common to *Geraniums*.

Garden performance: Plants of the new *Geranium* have been observed to have good garden performance and to tolerate rain, wind and temperatures from −19° C. to 35° C.

It is claimed:

1. A new and distinct *Geranium* plant named 'Blushing Turtle' as illustrated and described.

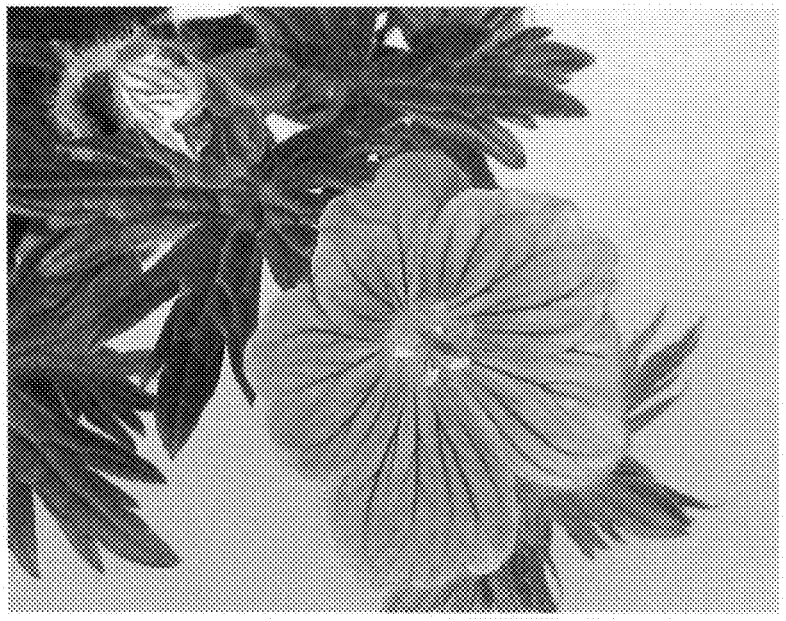
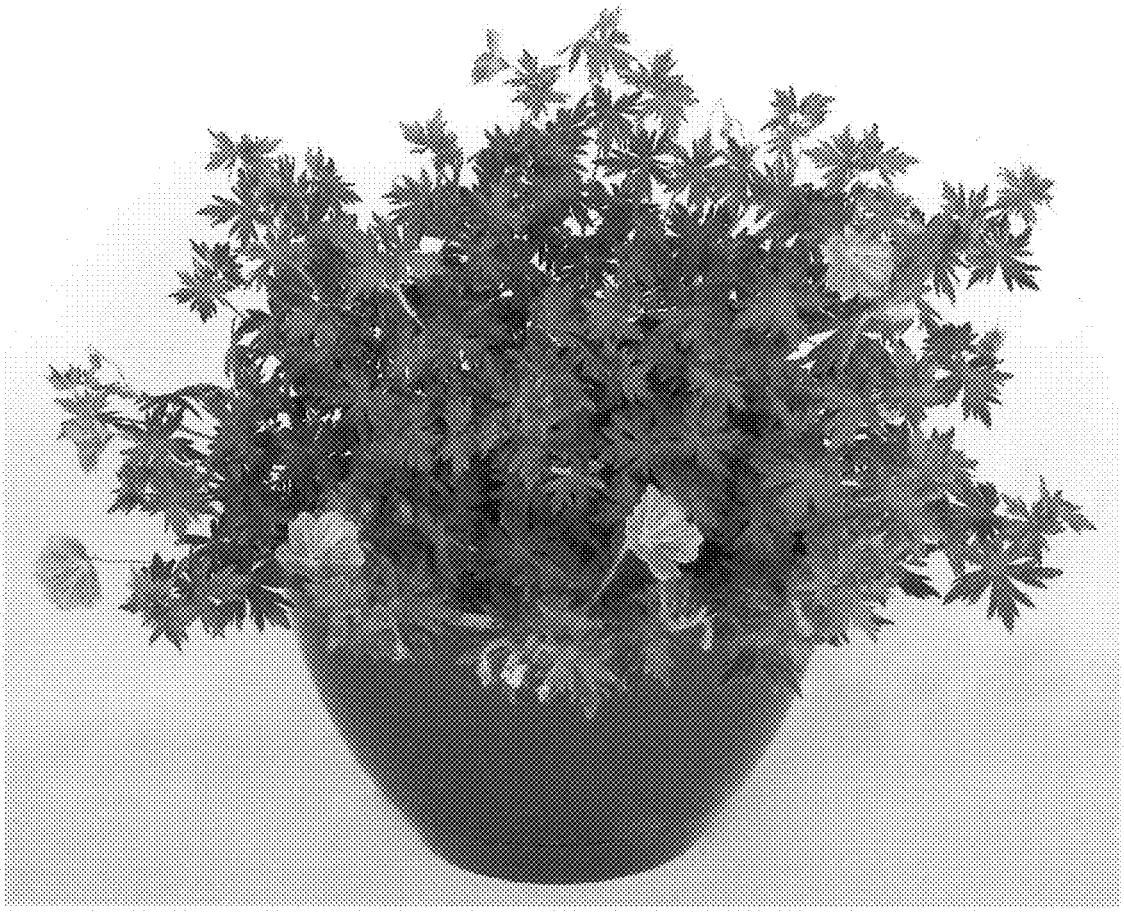

* * * * *